US012751650B2

(12) United States Patent
Ohashi et al.

(10) Patent No.: US 12,751,650 B2
(45) Date of Patent: Oct. 6, 2026

(54) MEDICAL APPARATUS TO BE PLACED ON THE SURFACE OF A LIVING BODY AND AN INDWELLING DEVICE THAT INCLUDES SUCH A MEDICAL APPARATUS

(71) Applicant: TERUMO KABUSHIKI KAISHA, Tokyo (JP)

(72) Inventors: Hirotaka Ohashi, Tokyo (JP); Ryoichi Sawazaki, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 899 days.

(21) Appl. No.: 18/163,025

(22) Filed: Feb. 1, 2023

(65) Prior Publication Data

US 2023/0181066 A1 Jun. 15, 2023

Related U.S. Application Data

(63) Continuation-in-part of application No. 17/389,712, filed on Jul. 30, 2021, now abandoned.

(30) Foreign Application Priority Data

Jul. 30, 2020 (JP) ................................ 2020-129412

(51) Int. Cl.
*A61B 5/145* (2006.01)
*A61B 5/00* (2006.01)

(52) U.S. Cl.
CPC ........ *A61B 5/14532* (2013.01); *A61B 5/4839* (2013.01); *A61B 5/6832* (2013.01)

(58) Field of Classification Search
CPC . A61B 5/6832; A61B 5/6833; A61B 5/68335; A61M 5/14244; A61M 5/14248;
(Continued)

(56) References Cited

U.S. PATENT DOCUMENTS 5,279,558 A * 1/1994 Kriesel ............... A61M 5/1409 604/890.1
2007/0021733 A1 1/2007 Hansen et al.
(Continued)

FOREIGN PATENT DOCUMENTS

CN 105592830 A 5/2016
CN 108883228 A 11/2018
(Continued)

OTHER PUBLICATIONS

Office Action/Search Report (First Office Action) issued on Mar. 15, 2025, in corresponding Chinese Patent Application No. 202110862583.9 and machine English translation of the Office Action. (11 pages).
(Continued)

*Primary Examiner* — Wesley G Harris
*Assistant Examiner* — Charles W Nichols
(74) *Attorney, Agent, or Firm* — BUCHANAN INGERSOLL & ROONEY PC

(57) ABSTRACT

A medical apparatus to be placed on the surface of a living body includes a main body, a main-body-side attaching sheet, and a plate-shaped intermediate member that is configured to be elastically deformable and is stacked between the main body and the main-body-side attaching sheet. The intermediate member includes a base, and a central piece and an arm piece extending in parallel from the base. The intermediate member is fixed to the main-body-side attaching sheet from the base to the central piece, and is fixed to the main body from the base to the arm piece. The central piece is not fixed to the main body, and the arm piece is not fixed to the attaching member.

21 Claims, 8 Drawing Sheets

(58) Field of Classification Search
CPC .. A61M 2025/0246; A61M 2025/0253; A61M 2025/0266; A61M 2025/0273
See application file for complete search history.

(56) References Cited

U.S. PATENT DOCUMENTS

| | | | | |
|---|---|---|---|---|
| 2009/0012472 | A1* | 1/2009 | Ahm | A61M 5/158 604/138 |
| 2014/0378799 | A1* | 12/2014 | Chattaraj | B32B 7/12 600/300 |
| 2019/0022306 | A1 | 1/2019 | Gibson et al. | |
| 2019/0030255 | A1 | 1/2019 | Iibuchi et al. | |
| 2022/0032012 | A1 | 2/2022 | Ohashi et al. | |

FOREIGN PATENT DOCUMENTS

| | | | |
|---|---|---|---|
| CN | 110115784 | A | 8/2019 |
| EP | 3437676 | A1 | 2/2019 |
| GB | 2423267 | A | 8/2006 |
| JP | 2007-509661 | A | 4/2007 |
| JP | 2013063105 | A | 4/2013 |
| JP | 2019-509787 | A | 4/2019 |
| WO | 2019/008529 | A1 | 1/2019 |

OTHER PUBLICATIONS

Office Action (Notice of Reasons for Refusal) issued Jun. 20, 2023, by the Japan Patent Office in corresponding Japanese Patent Application No. 2020-129412 and an English translation of the Office Action. (8 pages).

The European Search Report issued Dec. 21, 2021, by the European Patent Office in corresponding European Patent Application No. 21188481.2-1122, (4 pages).

* cited by examiner

MEDICAL APPARATUS TO BE PLACED ON THE SURFACE OF A LIVING BODY AND AN INDWELLING DEVICE THAT INCLUDES SUCH A MEDICAL APPARATUS

CROSS-REFERENCES TO RELATED APPLICATIONS

This application is a continuation-in-part of U.S. patent application Ser. No. 17/389,712 filed on Jul. 30, 2021 and claims priority to Japanese Patent Application No. 2020-129412 filed on Jul. 30, 2020, the entire content of both of which is incorporated herein by reference.

FIELD OF THE INVENTION

The present invention generally relates to a medical apparatus configured to be placed on the surface of a living body and an indwelling device includes such a medical apparatus and that is configured to be indwelled at the living body.

BACKGROUND DISCUSSION

Japanese Patent Application Publication No. 2013-63105 discloses a drug administration device (indwelling device) that is indwelled on a body surface in order to administer a drug solution into a body of a living body. The indwelling device includes a main body that supplies a drug solution, and an attaching sheet that is attached to a bottom surface of the main body and is attached to a body surface to indwell the main body.

SUMMARY

In order to enable this type of indwelling device to be attached to a body surface of various patients, a main body of the indwelling device has a flat bottom surface. However, when the main body is attached to a curved portion of a body surface, The ability to follow the contour of the body surface is deteriorated. Therefore, the main body may be peeled off or detached from the attaching member (or the attaching member may be peeled off from the body surface) in a case where the main body is indwelled for a long period of time or the like.

In order to address such a problem, in the indwelling device of Japanese Patent Application Publication No. 2013-63105, a case of the main body has a plastic region, and the case itself can be deformed in accordance with the curved shape of the body surface. However, in a case of a structure in which the case itself is deformed as described above, there are other problems such as complication of the device and an increase in manufacturing cost.

The indwelling device disclosed here can be stably indwelled on a body surface of a living body with a simple configuration.

One aspect of the disclosure here involves a medical apparatus that includes: a main body; a sheet-like attaching member for indwelling the main body on a body surface of a living body; and a plate-like intermediate member that is configured to be elastically deformable and is stacked between the main body and the attaching member, in which the intermediate member includes a base, and a first extending portion and a second extending portion that extend in parallel from the base, a first fixing portion fixed to the attaching member from the base to the first extending portion is provided on a surface of the intermediate member on a side of the attaching member, a second fixing portion fixed to the main body from the base to the second extending portion is provided on a surface of the intermediate member on a side of the main body, the first extending portion is not fixed to the main body, and the second extending portion is not fixed to the attaching member.

The above-described medical apparatus can be stably indwelled on a body surface of a living body with a simple configuration.

According to another aspect, a medical apparatus to be placed on a surface of a living body comprises a main body possessing a lower surface, an attaching sheet possessing an upper surface and a lower surface, and an elastically deformable intermediate member positioned between the attaching sheet and the main body. The upper surface of the attaching sheet faces towards the lower surface of the main body, and the lower surface of the attaching sheet is provided with an adhesive to adhere to the surface of the living body. The intermediate member is positioned in a plane and includes an upper surface facing towards the main body and a lower surface facing towards the attaching sheet. The intermediate member includes a base, and also includes first and second extending portions that extend away from the base and that are parallel to one another, with the first and second extending portions being movable relative to one another and in opposite directions out of the plane. A first fixing portion is positioned between the intermediate member and the attaching sheet, and the first fixing portion is fixed to at least a part of the upper surface of the attaching sheet and to the lower surface of the base of the intermediate member so that the base of the intermediate member is fixed to the attaching sheet. A second fixing portion is positioned between the intermediate member and the main body, and the second fixing portion is fixed to at least a part of the upper surface of the base of the intermediate member and to the lower surface of the main body so that the base of the intermediate member is fixed to the main body. The first extending portion is fixed to the attaching sheet and is movable relative to the main body, and the second extending portion is fixed to the main body and is movable relative to the attaching member.

In accordance with another aspect, a drug administration device comprises a drug supply source, a tube connectable to the drug supply source, and an administration unit connectable to the tube and configured to administer a drug solution from the drug supply source and through the tube when the tube is connected to both the drug supply source and the administration unit. The drug supply source includes a main body possessing a lower surface to face toward a surface of a living body, an attaching sheet possessing an upper surface and a lower surface, and an elastically deformable intermediate member positioned between the main body and the attaching sheet. The upper surface of the attaching sheet faces towards the lower surface of the main body, and the lower surface of the attaching sheet is adapted to face towards the surface of the living body. The intermediate member includes a base, a first extending portion and a second extending portion, with the first and second extending portions extending parallel to one another and away from the base. A first fixing portion is fixed to the lower surface of the base of the intermediate member and to the upper surface of the attaching sheet, and a second fixing portion is fixed to the upper surface of the base of the intermediate member and to the lower surface of the main body. The first extending portion is not fixed to the main body; and the second extending portion being not fixed to the attaching member.

DETAILED DESCRIPTION

Set forth below with reference to the accompanying drawings is a detailed description of embodiments of a medical apparatus that is configured to be placed on the surface of a living body, an indwelling device that includes the medical apparatus and method of use representing examples of the inventive medical apparatus, indwelling device and method disclosed here.

Figure 1:
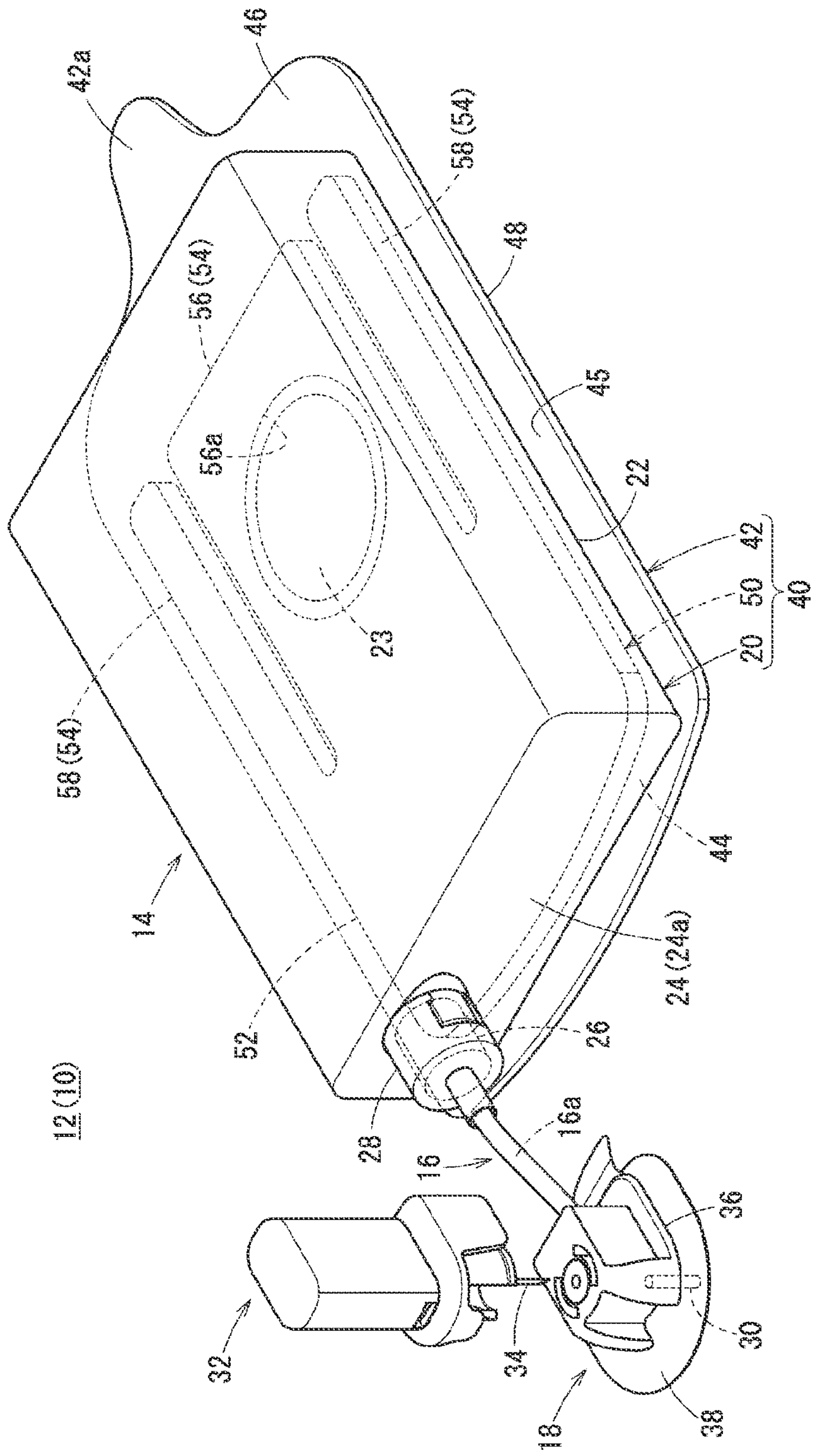
FIG. 1 is a perspective view showing an overall configuration of an indwelling device (drug administration device) according to an embodiment of the present invention.

As an indwelling device 10 according to one embodiment disclosed as an example of the indwelling device, a drug administration device 12 shown in FIG. 1 will be representatively described. The drug administration device 12 is a medical device that is indwelled or positioned on a body surface of a patient by a medical worker or the like and automatically administers a drug into the body in an indwelled state. The indwelling device 10 according to the present invention is not limited to the drug administration device 12, and can be applied to various devices indwelled on a body surface of a living body. Examples of the device include a component measurement device such as a blood glucose meter, a biosensor or another medical device, and a terminal other than medical devices such as an information processing device and a communication device.

The drug administration device 12 includes a main body 14 that is a drug supply source, a tube 16 connected to the main body 14, and an administration unit 18 connected to the tube 16 and configured to administer a drug solution supplied from the tube 16 to a patient. That is, in the drug administration device 12, the main body 14 and the administration unit 18 are connected to each other via the tube 16, thereby ensuring a certain degree of mutual freedom. Therefore, the drug administration device 12 can easily and accurately position the main body 14 and the administration unit 18 at desired positions on the body surface when indwelled in a living body.

The main body 14 of the drug administration device 12 includes a container for storing a drug, a mechanism unit that delivers the drug from the container to the tube 16 at an appropriate timing, a control unit that controls operation of the mechanism unit, a power source of the mechanism unit and the control unit (both not shown), and the like. Examples of the drug administered by the drug administration device 12 include liquid drugs such as antibody drugs, anticancer agents, chemotherapeutic agents, anesthetics, antibiotics, insulin, blood products, and nutrients. The main body 14 has a case 20 that accommodates these components.

The case 20 has a large rectangular shape in plan view, and is configured as a substantially rectangular housing having a low rectangular shape in a thickness direction. The size of the case 20 is set to, for example, a range in which a length in a longitudinal direction is about 30 mm to 150 mm, a range in which a length in a lateral direction is about 10 mm to 100 mm, and a range in which the thickness is about 5 mm to 20 mm.

In the case 20, a bottom surface 22 which is a side that faces the surface of the living body (a fixing target place) is formed in a flat shape. The bottom surface 22 may be formed in a slightly curved surface according to the shape of the body surface to which the medical apparatus is applied. The four side portions of the bottom surface 22 are continuous in an arc or rounded shape with respect to the four side surface portions 24 of the case 20, and corner portions where the side portions intersect each other are also formed in an arc or rounded shape. The case 20 (main body 14) constitutes a part of the medical apparatus 40, and is positioned on (adhered to) the body surface of the living body.

The bottom surface 22 is provided with an operation unit 23 for operating the main body 14. The operation unit 23 according to the present embodiment is configured as a round push button. The main body 14 is configured such that the power source is turned off in the product providing state (i.e., prior to use when the product is supplied or provided to the user), and the control unit continues the operation of the main body 14 after being turned on once by the pressing of the operation unit 23 by the user. The operation unit 23 is not limited to the one that performs the on/off operation of the power supply, and can be applied to various configurations for operating the indwelling device 10. The main body 14 may be provided with the operation unit 23 at a location other than the bottom surface 22 of the case 20, and may be configured not to be provided with the operation unit 23 when operated by external communication or the like.

The case 20 is preferably made of a hard resin material so as not to be elastically deformable. The resin material of the case 20 is not particularly limited, but for example, a thermoplastic resin such as polyacetal, polyamide, polyester, polycarbonate, polysulfone, polytetrafluoroethylene, polyphenylene sulfide, or polypropylene may be applied. The shape of the case 20 is not limited to a substantially rectangular shape, and various shapes such as a cubic shape, a hemispherical shape, and other three-dimensional shapes can be adopted.

A main-body-side connector 26 for connecting to the tube 16 is provided at one end in the longitudinal direction (direction of arrow A) of the case 20. The main-body-side connector 26 protrudes a short distance or amount from a side surface portion 24*a* on one end side of the case 20. A mounting structure for mounting the tube 16 is formed on an outer circumferential surface of the main-body-side connector 26.

The tube 16 of the drug administration device 12 is a flexible tube having a flow passage 16*a* therein which extends by a predetermined length and through which the drug can flow. The length of the tube 16 is not particularly limited, but is set in a range of about 10 mm to 100 mm, for example. A tube side connector 28 attachable to and detachable from the main-body-side connector 26 is fixed to one end portion of the tube 16. The administration unit 18 is fixed to the other end of the tube 16.

The tube side connector 28 includes a hollow needle (not shown). The hollow needle allows a storage space of the container and the flow passage 16*a* of the tube 16 to communicate with each other in a state where the tube side connector 28 is mounted to the main-body-side connector 26.

The administration unit 18 of the drug administration device 12 administers a drug to a patient via a catheter 30 inserted into the body (subcutaneously) from the body surface. Before the catheter 30 is indwelled in the patient, the administration unit 18 is assembled to an insertion device 32, and an inner needle 34 of the insertion device 32 penetrates the catheter 30 (FIG. 1 shows a separated state of the administration unit 18 and the insertion device 32 for ease of understanding of the present invention). A user punctures the body in a state in which the catheter 30 and the inner needle 34 overlap, and withdraws the inner needle 34 from the catheter 30 in the punctured state (detaches the insertion device 32 from the administration unit 18), thereby indwelling the catheter 30 in the patient.

Specifically, the administration unit 18 includes a catheter 30, a hub 36 that holds a proximal end of the catheter 30 and to which the tube 16 is coupled, and an administration unit side attaching sheet 38 that attaches the hub 36 onto the body surface.

Figure 2:
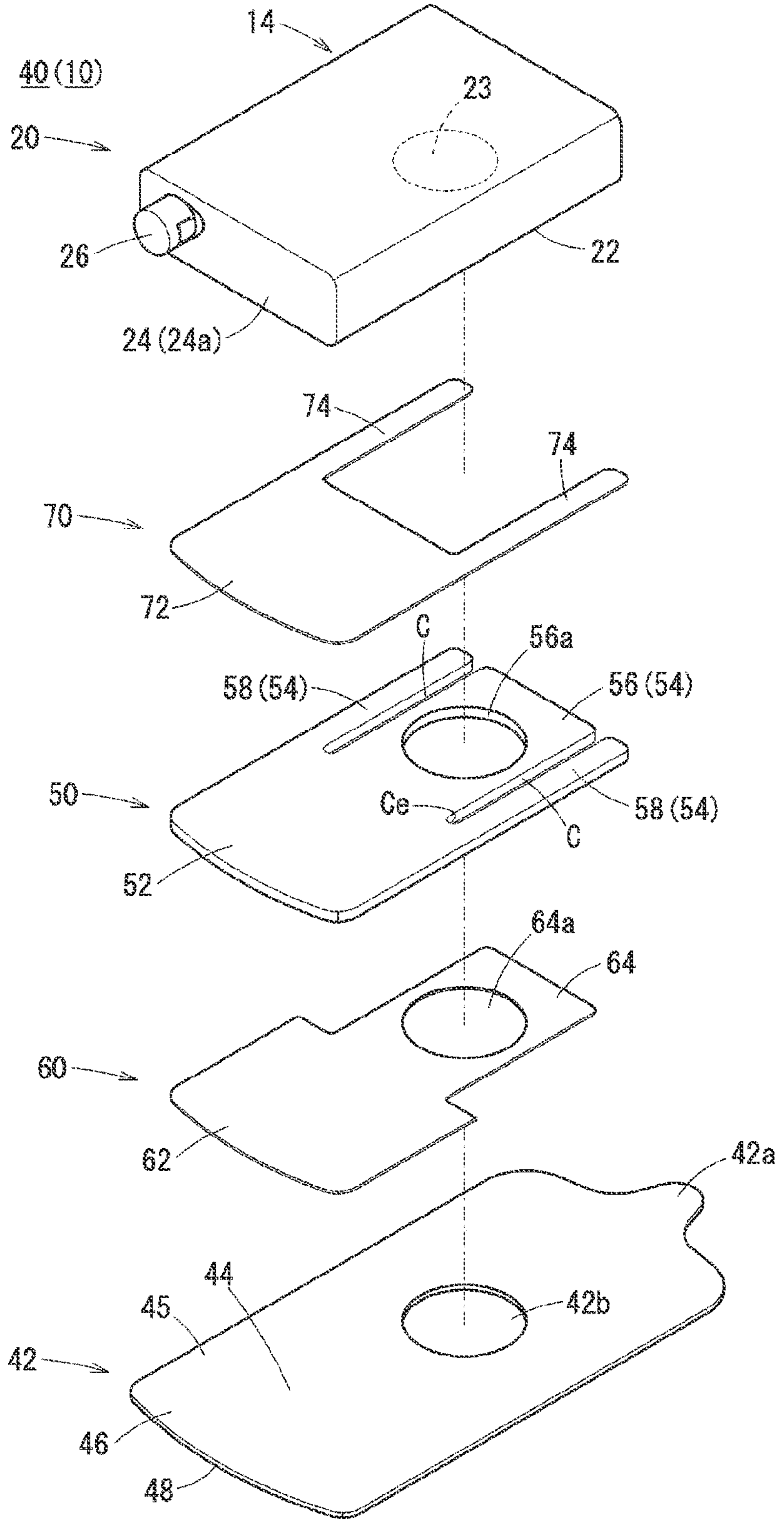
FIG. 2 is an exploded perspective view showing a medical apparatus that is positionable on the surface of a living body and forms part of the indwelling device.
Figure 3:
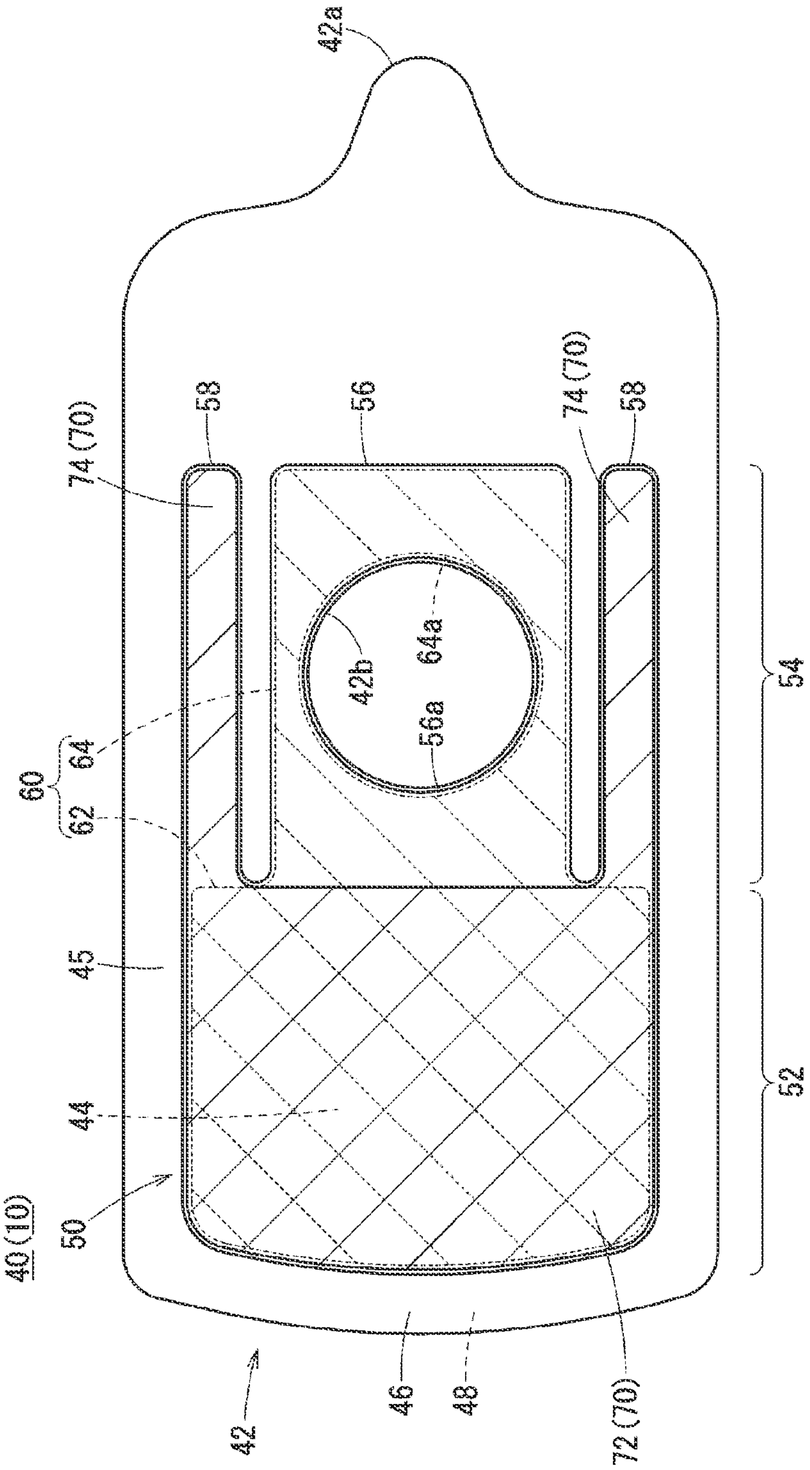
FIG. 3 is a plan view showing a state in which a main-body-side attaching sheet, an intermediate member, a lower adhesive body, and an upper adhesive body are stacked.

Next, the medical apparatus 40 in which the main body 14 of the drug administration device 12 (the indwelling device 10) is positioned or placed on (adhered to) the surface of the living body will be described with reference to FIGS. 1 to 3. The medical apparatus 40 includes the case 20 of the main body 14, a sheet-shaped or sheet-like main-body-side attaching sheet 42 (attaching member) for attaching the main body 14 to the body surface of the living body, and a plate-shaped or plate-like intermediate member 50 stacked (positioned) between the main body 14 and the main-body-side attaching sheet 42.

The main-body-side attaching sheet 42 has a substantially rectangular shape in plan view corresponding to the shape of the bottom surface 22 of the case 20, and has flexibility capable of following the body surface (i.e., the main-body-side attaching sheet 42 is able to generally conform to the surface of the body). The main-body-side attaching sheet 42 is formed to be longer than the bottom surface 22 of the main body 14 in both the longitudinal direction and the lateral direction. Both sides in the longitudinal direction of the main-body-side attaching sheet 42 (shorter sides in FIG. 2) are formed in an arc shape in which the central portion in the lateral direction is slightly expanded. Both sides in the lateral direction of the main-body-side attaching sheet 42 are connected to both sides in the longitudinal direction with rounded corners interposed therebetween, and extend in parallel and linearly with each other.

A pair of corners located at one end in the longitudinal direction of the main-body-side attaching sheet 42 is formed into a round corner having a small (relatively smaller) radius of curvature. A pair of corners located at the other end in the longitudinal direction of the main-body-side attaching sheet 42 is formed into a round corner having a large (relatively larger) radius of curvature. A short protrusion 42*a* is continuously provided at the central portion in the lateral direction of the other end in the longitudinal direction of the main-body-side attaching sheet 42. An attaching member side exposure hole 42*b* that exposes the operation unit 23 of the case 20 is provided slightly closer to the longitudinal direction end than the central portion in the longitudinal direction of the main-body-side attaching sheet 42. That is, with reference to the longitudinal direction of the main-body-side attaching sheet 42 in FIG. 2, the attaching member side exposure hole 42*b* is located closer to one of the longitudinal ends The upper surface of the main-body-side attaching sheet 42 has a fixing region 44 of the main body 14 in a range from one end in the longitudinal direction to beyond the central portion in the longitudinal direction. The fixing region 44 coincides with the fixing range of the intermediate member 50. The main-body-side attaching sheet 42 has a margin region 45 for exposing the upper surface of the main-body-side attaching sheet 42 around the fixing region 44 in the fixed state of the main body 14. The margin region 45 is formed to be narrow on one end side in the longitudinal direction and both end sides in the lateral direction, and formed to be wide on the other end side in the longitudinal direction.

The main-body-side attaching sheet 42 is formed by stacking (layering or laminating) a base material 46 and an adhesive layer 48. An appropriate material is preferably applied to the base material 46 in consideration of stretchability, followability, air permeability, and the like. Examples of the material of the base material 46 include polyethylene, polyester, polyurethane, nylon, polyolefin, cotton fabric, woven fabric, and nonwoven fabric. The base material 46 may be configured to have functions such as water repellency, hydrophilicity, irregularities, air holes, moisture permeability, and flexibility by arbitrary processing.

The adhesive layer 48 is formed on the entire lower surface (one surface) of the main-body-side attaching sheet 42 facing the body surface. As a material of the adhesive layer 48, for example, an acrylic adhesive, a silicone-based adhesive, a urethane-based adhesive, a synthetic rubber-based adhesive, or the like is applied. The lower surface of the main-body-side attaching sheet 42 may have not only the adhesive layer 48 provided on the entire surface but also a non-adhesive region where the adhesive layer 48 is not applied to a part of the lower surface (for example, the protrusion 42*a*).

The intermediate member 50 is a flat plate-shaped member that is attached to the bottom surface 22 of the main body 14 and attached to the main-body-side attaching sheet 42. Therefore, the medical apparatus 40 includes a lower adhesive body 60 (first fixing portion) that fixes the main-body-side attaching sheet 42 and the intermediate member 50, and the upper adhesive body 70 (second fixing portion) that fixes the case 20 of the main body 14 and the intermediate member 50. The lower adhesive body 60 is provided on the lower surface (one surface) of the intermediate member 50. The upper adhesive body 70 is provided on the upper surface (the other surface) of the intermediate member 50.

The intermediate member 50 is formed sufficiently thinner than the thickness of the case 20, and can be elastically deformed (curved) such that the plate surface is warped. The thickness of the intermediate member 50 is not particularly limited, but may be set in a range of, for example, about 0.1 mm to 3 mm. For example, the elastic modulus of the intermediate member 50 is preferably set to be larger than the elastic modulus of the body surface (or to the same extent or to a slightly smaller extent).

The intermediate member 50 has a substantially rectangular shape corresponding to the shape of the case 20 (bottom surface 22) in plan view. The planar shape of the intermediate member 50 is formed to match (or resemble to be slightly smaller than) the bottom surface 22 of the main body 14. The intermediate member 50 includes a base 52 constituting a substantially half of one end side in the longitudinal direction of the intermediate member 50 and a plurality of elastic pieces 54 constituting a substantially half of the other end side in the longitudinal direction of the intermediate member 50. In the longitudinal direction of the intermediate member 50, the ratio of the length of each of the base 52 and the plurality of elastic pieces 54 to the entire length of the intermediate member 50 is not particularly limited. In the longitudinal direction of the intermediate member 50, for example, the length of the base 52 may be set in a range of 20% to 80% of the length of the intermediate member 50, and the lengths of the plurality of elastic pieces 54 may be set according to a ratio of the length of the base 52 to the length of the intermediate member 50.

The base 52 is attached to substantially a half of one end side in the longitudinal direction of the case 20 (bottom surface 22) and attached to substantially a half of one end side in the longitudinal direction of the main-body-side attaching sheet 42. Therefore, as shown in FIG. 2, the lower surface of the base 52 is attached to the lower adhesive body 60, and the upper surface of the base 52 is attached to the upper adhesive body 70. A pair of corners on one end side in the longitudinal direction of the base 52 is formed into a round corner matching the shape of the bottom surface 22. The base 52 is disposed at a position in the vicinity of the main-body-side connector 26 (one end side of the main body 14), so that it is possible to enhance the attachment of the outflow portion of the drug of the main body 14 via the main-body-side attaching sheet 42.

The plurality of elastic pieces 54 include a central piece 56 provided at the center in the lateral direction of the intermediate member 50 and a pair of arm pieces 58 provided on both sides in the lateral direction of the central piece 56. Each of the central piece 56 and the pair of arm pieces 58 is flush with the base 52 (i.e., the upper surfaces of the central piece 56 and the arm pieces 58 are planar with the upper surface of the base 52, and the lower surfaces of the central piece 56 and the arm pieces 58 are planar with the lower surface of the base 52). A clearance C is provided between the central piece 56 and the pair of arm pieces 58 to separate them from each other. The central piece 56 thus has two longitudinally extending side surfaces, one of which faces a longitudinally extending side surface of one of the arm pieces 58 and the other of which faces a longitudinally extending side surface of the other arm piece 58. Thus, the elastic pieces 54 (56, 58, 58) are movable relative to one another (including opposite directions) out of the plane of the intermediate member 50 (base 52).

The central piece 56 is formed in a rectangular shape extending from the other end side of the base 52 toward the other end side in the longitudinal direction of the intermediate member 50 by a predetermined length. For example, the width of the central piece 56 in the lateral direction is set to be wide in a range of about 2 to 10 times the width of one arm piece 58.

In the medical apparatus 40, the central piece 56 constitutes a first extending portion that is attached to the main-body-side attaching sheet 42 but is not attached to the case 20 (bottom surface 22). Therefore, the lower adhesive body 60 is attached to the lower surface of the central piece 56, while the upper adhesive body 70 is not attached to the upper surface of the central piece 56.

The surface of the central piece 56 is provided with an intermediate member side exposure hole 56*a* that is formed to have a larger diameter than the attaching member side exposure hole 42*b* and exposes the operation unit 23. The intermediate member 50 is attached to the main-body-side attaching sheet 42 such that the attaching member side exposure hole 42*b* is accommodated inside the intermediate member side exposure hole 56*a*.

The pair of arm pieces 58 is formed in a long plate shape extending from the other end side of the base 52 toward the other end side in the longitudinal direction of the intermediate member 50 by the same length as the central piece 56. The extension length of the pair of arm pieces 58 may be different from the extension length of the central piece 56. In the pair of arm pieces 58, the outer side in the width direction is linearly continuous with one lateral side and the other lateral side of the base 52.

The pair of clearances C provided between the central piece 56 and the pair of arm pieces 58 is set to a width smaller than the width of the pair of arm pieces 58, for example, and extends along the longitudinal direction of the intermediate member 50. An arc-shaped edge portion or end portion Ce in contact with the base 52 is formed at one end of the clearance C (a root portion where the central piece 56 and the pair of arm pieces 58 are coupled to the base 52).

The pair of arm pieces 58 is not attached to the main-body-side attaching sheet 42, but constitutes a second extending portion of the medical apparatus 40 attached to the case 20 (bottom surface 22). Therefore, the lower adhesive body 60 is not attached to the lower surface of the arm piece 58, while the upper adhesive body 70 is attached to the upper surface of the arm piece 58.

Examples of the constituent material of the intermediate member 50 include polymer materials such as polyethylene, polypropylene, polyethylene terephthalate, polyvinyl chloride, polystyrene, ABS resin, acrylic, polyamide, polyester, and fluororesin, or mixtures thereof.

The lower adhesive body 60 is a double-sided tape having adhesive layers on a lower surface and an upper surface thereof. The upper adhesive body 70 is a double-sided tape having adhesive layers on a lower surface and an upper surface thereof. The lower adhesive body 60 and the upper adhesive body 70 are formed in a sheet shape thinner than the thickness of the intermediate member 50, and have flexibility. The lower adhesive body 60 and the upper adhesive body 70 may be configured by directly applying an adhesive (for example, the materials mentioned for the adhesive layer 48 of the main-body-side attaching sheet 42) to the lower surface and the upper surface of the intermediate member 50.

The lower adhesive body 60 has a lower base attaching region 62 attached to the entire lower surface of the base 52 and a lower elastic piece attaching region 64 attached to the entire lower surface of the central piece 56. The lower base attaching region 62 and the lower elastic piece attaching region 64 are continuous with the same thickness. The lower elastic piece attaching region 64 has an adhesive-member-side exposure hole 64*a* at a position corresponding to the intermediate member side exposure hole 56*a*. The lower base attaching region 62 only needs to firmly fix the main-body-side attaching sheet 42 and the base 52, and may be partially provided on the lower surface of the base 52. Similarly, the lower elastic piece attaching region 64 may also be partially provided on the lower surface of the central piece 56.

The upper adhesive body 70 has an upper base attaching region 72 attached to the base 52 and a pair of upper elastic piece attaching regions 74 attached to the pair of arm pieces 58. The upper base attaching region 72 and the pair of upper elastic piece attaching regions 74 are continuous with each other with the same thickness. The upper base attaching region 72 only needs to firmly fix the main body 14 and the base 52, and may be partially provided on the upper surface of the base 52. Similarly, the pair of upper elastic piece attaching regions 74 may also be partially provided on the upper surfaces of the pair of arm pieces 58.

Next, a state where the main-body-side attaching sheet 42, the intermediate member 50, the lower adhesive body 60, and the upper adhesive body 70 are attached will be described with reference to FIG. 3. The intermediate member 50 is attached to the main-body-side attaching sheet 42 by the lower adhesive body 60. However, as described above, in the intermediate member 50, the base 52 and the central piece 56 are attached to the main-body-side attaching sheet 42, but the pair of arm pieces 58 is not attached to the main-body-side attaching sheet 42. The intermediate member 50 (the base 52 and the central piece 56) harder than the main-body-side attaching sheet 42 can hold a wide range of the plane of the main-body-side attaching sheet 42 and suppress wrinkles and slack of the main-body-side attaching sheet 42.

In the intermediate member 50, the base 52 and the pair of arm pieces 58 are attached to the case 20, but the central piece 56 is not attached to the case 20. In this case, in the intermediate member 50, the pair of arm pieces 58 is attached to the vicinities of both sides in the lateral direction of the case 20, so that the attaching state of the case 20 and the intermediate member 50 can be stabilized, and displacement of the case 20 can be suppressed.

The drug administration device 12 (the indwelling device 10) according to the present embodiment is basically configured as described above, and its operation will be described below.

The drug administration device 12 is provided to the user in a state where, while the administration unit 18 and the insertion device 32 are assembled, the tube 16 coupled to the administration unit 18 and the main body 14 are separated. For example, at the time of indwelling the drug administration device 12, the user sequentially performs an administration unit indwelling step of indwelling the administration unit 18, a connecting step of connecting the tube 16 coupled to the administration unit 18 and the main body 14, and a main body placing (adhering) step of placing (adhering) the main body 14 on the living body surface. These operational steps do not necessarily have to be performed in the above order, and the order of performing the operational steps may be changed as appropriate.

By the above-described method, the main body 14 of the drug administration device 12 is fixed on the body surface via the medical apparatus 40. At the time of indwelling, the main body 14 is activated based on ON operation of the operation unit 23. At this time, since the operation unit 23 is exposed through the attaching member side exposure hole 42*b* and the intermediate member side exposure hole 56*a*, the user can easily operate the operation unit 23. Even if the operation of the operation unit 23 is forgotten and the main-body-side attaching sheet 42 is attached to the body surface, the operation unit 23 can be exposed by curving the central piece 56 without peeling the main-body-side attaching sheet 42 from the body surface.

After being indwelled, the drug administration device 12 automatically administers the drug to the patient under the control of the control unit. The indwelling period (administration period of the drug) of the drug administration device 12 is set to, for example, a range of about one week to four weeks.

After being indwelled or positioned on the surface of the patient's body, the drug administration device 12 may automatically administer a drug to the patient under control of the control unit after a predetermined time has elapsed. The drug administration device 12 is controlled so that drug administration is started when the predetermined time has elapsed after a medical practice or medical procedure (for example, diagnosis, examination, surgery, drug administration, etc.) is finished. The predetermined time may be appropriately set in consideration of the medical practice/procedure, a type of a drug to be administered after the medical practice/procedure, and the like. Examples of the predetermined time include at least 0.5 hour, preferably at least 1.0 hour, and a range of several hours to several tens of hours.

For example, a patient undergoing anticancer drug therapy may show side effects after administration of the anticancer drug. Therefore, in order to suppress the side effects, the patient may need additional administration of another drug after a predetermined time (for example, after several hours) has elapsed subsequent to the administration of the anticancer drug. If such additional administration is required, the patient must remain in a hospital until a predetermined time has elapsed after administration of the anticancer drug, or must visit the hospital again the next day or later, which is a heavy burden on the patient. Thus, the drug administration device 12 disclosed here can be used to administer a drug at a location different from (geographically different from or miles away from) the medical facility at which the medical practice or medical procedure was performed.

As described above, the drug administration device is controlled so that administration of the drug may be started after the lapse of the predetermined time. The patient can thus go home with the drug administration device placed on the body surface or indwelled, and is able to receive the additional administration like that described above while staying at home.

Figure 4A:
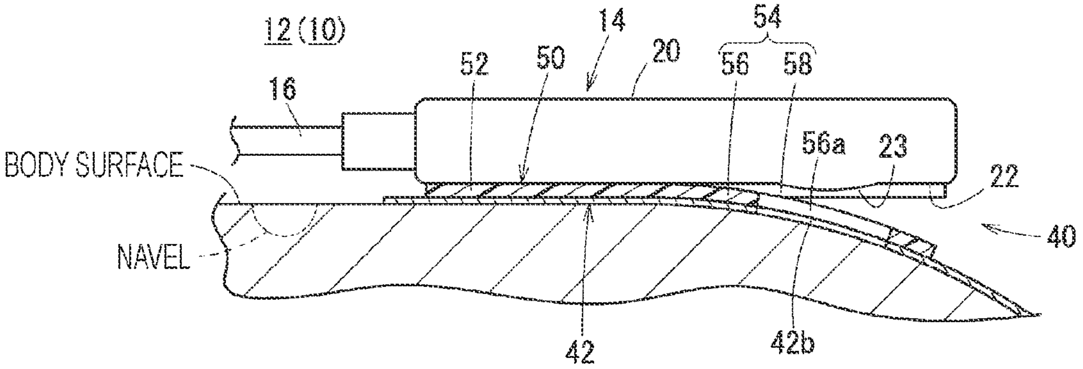
FIG. 4A is a side cross-sectional view showing the medical apparatus, including the main body, positioned or placed on a body surface of a living body.
Figure 4B:
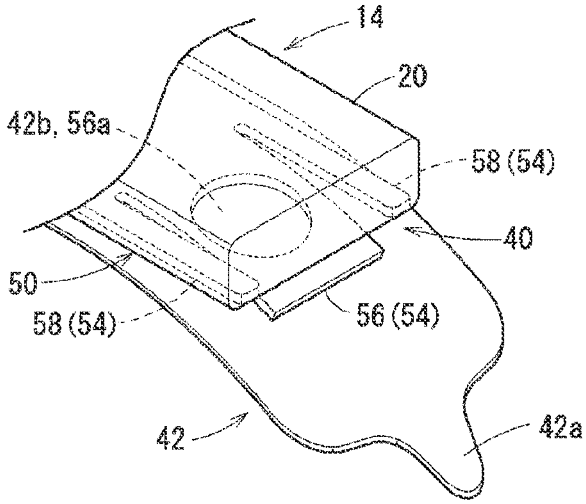
FIG. 4B is a partial perspective view showing positions of the main body and the main-body-side attaching sheet placed on and attached (e.g., adhered) to the surface of the living body.

For example, as shown in FIGS. 4A and 4B, in the attached or adhered state of the main body 14, the main-body-side attaching sheet 42 is attached to a curved portion of the abdomen (body surface) of the patient. At this time, the base 52 of the intermediate member 50 fixed to both the main body 14 and the main-body-side attaching sheet 42 faces the body surface in a narrow range of about half of the entire length of the intermediate member 50 in the longitudinal direction. The entire one end side of the main-body-side attaching sheet 42 including the fixing region 44 of the base 52 and the margin region 45 on the one end side is in close contact with the body surface. In particular, the drug administration device 12 is indwelled so that one end side of the main body 14 faces the center (navel) side of the abdomen at a substantially flat portion of the abdomen, and thereby the case 20 can be stably fixed. One end side of the main body 14 is firmly fixed to the main-body-side attaching sheet 42 via the base 52 of the intermediate member 50. Therefore, for example, the intermediate member 50 can release a load applied from the tube 16 to the main-body-side attaching sheet 42 from one end side to the other end side.

In the attached (adhered) state, the central piece 56 on the other end side of the intermediate member 50 can be separated from the main body 14, and is disposed close to the body surface (the main-body-side attaching sheet 42) following the curve of the body surface. Conversely, the pair of arm pieces 58 of the intermediate member 50 can be separated (floated) from the main-body-side attaching sheet 42 while maintaining the fixed state with the bottom surface 22 of the case 20 without following the body surface.

That is, in the medical apparatus 40, while both the case 20 and the body surface are fixed at the base 52, the central piece 56 follows only the body surface (the main-body-side attaching sheet 42), and the pair of arm pieces 58 follows only the case 20. As a result, the other end side (the plurality of elastic pieces 54 side) of the intermediate member 50 is able to approach and separate from the body surface.

Figure 4C:
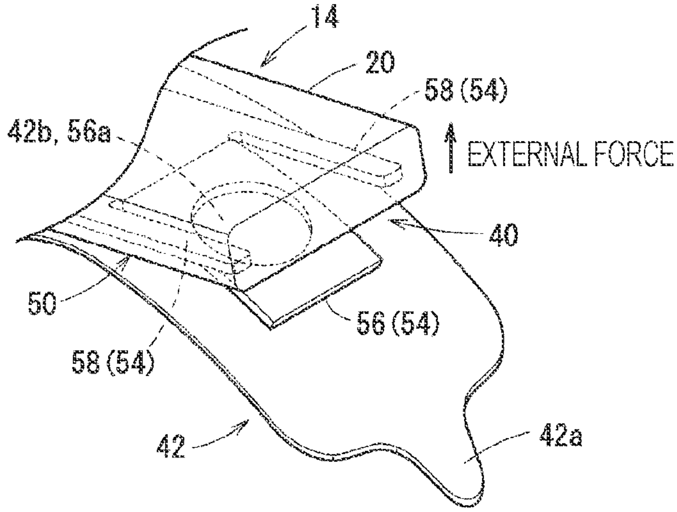
FIG. 4C is a partial perspective view showing operation when an external force is applied to the main body.

In the medical apparatus 40 positioned on the surface of a living body as described above, even if an external force that tends to peel the main body 14 from the body surface (the main-body-side attaching sheet 42) is applied to the main body 14 due to daily life, unexpected contact, or the like, the intermediate member 50 is elastically deformed, so that peeling can be avoided. For example, as shown in FIG. 4C, a case where an external force that separates the other end side of the case 20 from the body surface is applied will be described. In this case, the portion of the intermediate member 50 fixed to the main body 14 from the base 52 to each arm piece 58 is prevented from peeling from the main body 14. The portion of the intermediate member 50 fixed to the main-body-side attaching sheet 42 from the base 52 to the central piece 56 is prevented from peeling off from the main-body-side attaching sheet 42.

Therefore, even if the case 20 is separated from the body surface by an external force, the intermediate member 50 is elastically deformed as appropriate while being fixed to the main body 14 and the main-body-side attaching sheet 42. In the elastic deformation, while the coupling is continued at the base 52, the central piece 56 and the pair of arm pieces 58 are separated from each other to release an external force. At the time of elastic deformation of the elastic piece 54, the arc-shaped edge portion Ce of the base 52 where the central piece 56 and the pair of arm pieces 58 are coupled can suppress breakage of the intermediate member 50 even when an external force that tears the central piece 56 and the pair of arm pieces 58 is applied.

As described above, even in a case where the main body 14 is applied (adhered) to the living body surface for a long period of time, the drug administration device 12 can greatly reduce peeling or separation of the main-body-side attaching sheet 42 from the body surface. In particular, the rectangular main body 14 is easily peeled off along the longitudinal direction in the indwelling state, but since the elastic piece 54 is provided on the other end side in the longitudinal direction, the range in which the main body 14 and the main-body-side attaching sheet 42 are attached together is narrowed, and peeling of the main body 14 can be suppressed.

The drug administration device 12 having the medical apparatus 40 was attached to the abdomen of the examiner for 30 hours, and then an evaluation test of observing the attaching state was performed. As a result of the evaluation test, in the medical apparatus 40, about 5% of the entire area of the main-body-side attaching sheet 42 was peeled off, but it was confirmed that the main body 14 itself was not peeled off and the attached (adhered) state could be preferably maintained.

The present invention is not limited to the above embodiments, and various modifications can be made in accordance with the gist of the invention. Hereinafter, some modifications of the indwelling device 10 according to the present invention will be described. In the description below, features that are the same or similar to those described above are identified by the same reference numerals and a detailed description of such features is not repeated.

First Modification

Figure 5:
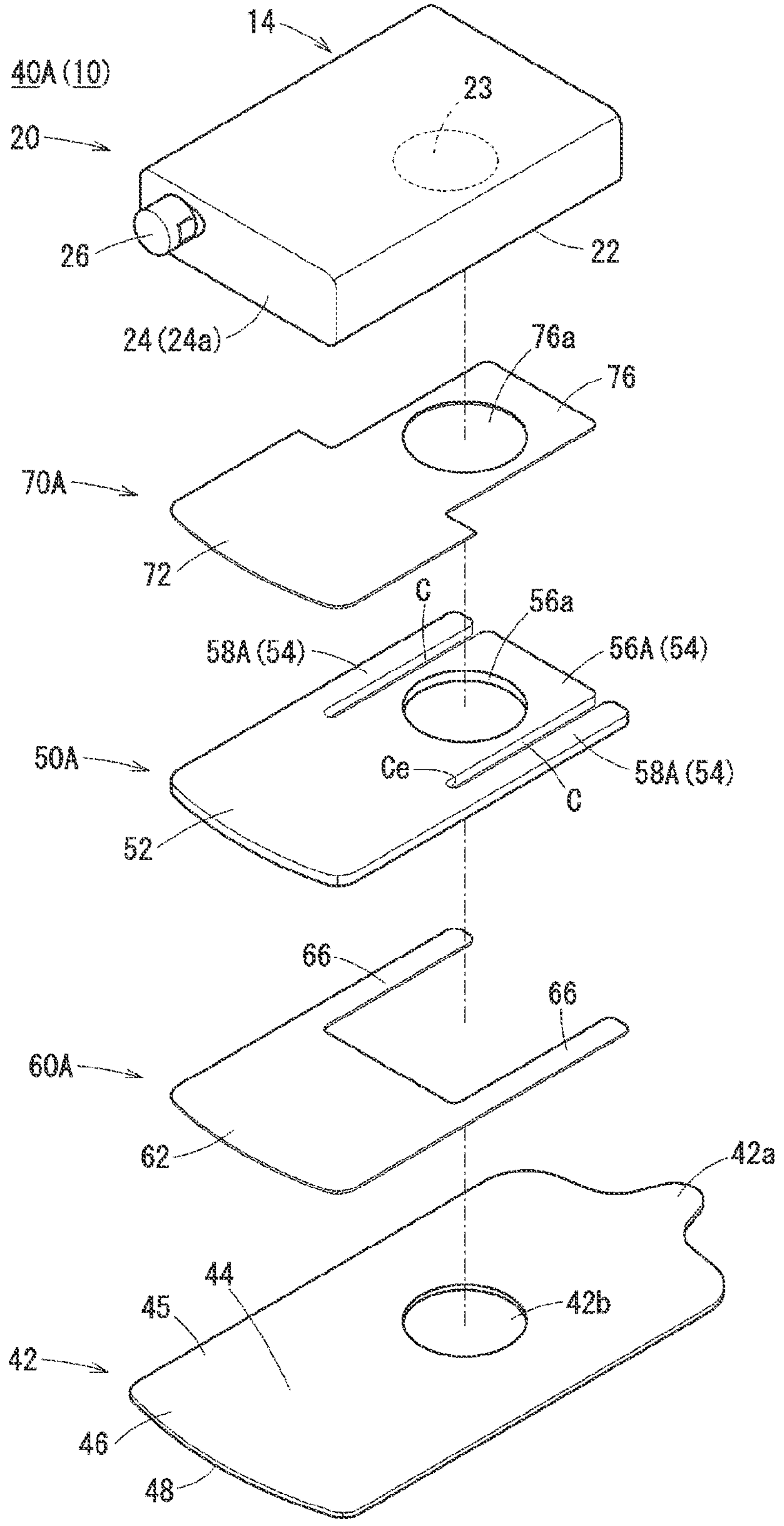
FIG. 5 is an exploded perspective view showing a medical apparatus according to a first modification.

A medical apparatus 40A (intermediate member 50A) of the indwelling device 10 according to a first modification shown in FIG. 5 is different from the above-mentioned medical apparatus 40 in that it has a central piece 56A fixed to the main body 14, and has a pair of arm pieces 58A fixed to the main-body-side attaching sheet 42. In this case, the lower adhesive body 60A has a lower base attaching region 62 and a lower elastic piece attaching region 66 continuous with the lower base attaching region 62 and facing the pair of arm pieces 58A. Conversely, the upper adhesive body 70A has an upper base attaching region 72 and an elastic piece attaching region 76 continuous with the upper base attaching region 72 and facing the central piece 56A. In this case, the elastic piece attaching region 76 has the adhesive exposure hole 76*a*.

Even with such a configuration, in the medical apparatus 40A, while the pair of arm pieces 58A follows the body surface in the attached (adhered) state of the main body 14, the central piece 56A follows the main body 14. Then, the central piece 56A and the pair of arm pieces 58A are relatively elastically deformed, so that it is possible to resist an external force.

Second Modification

Figure 6:
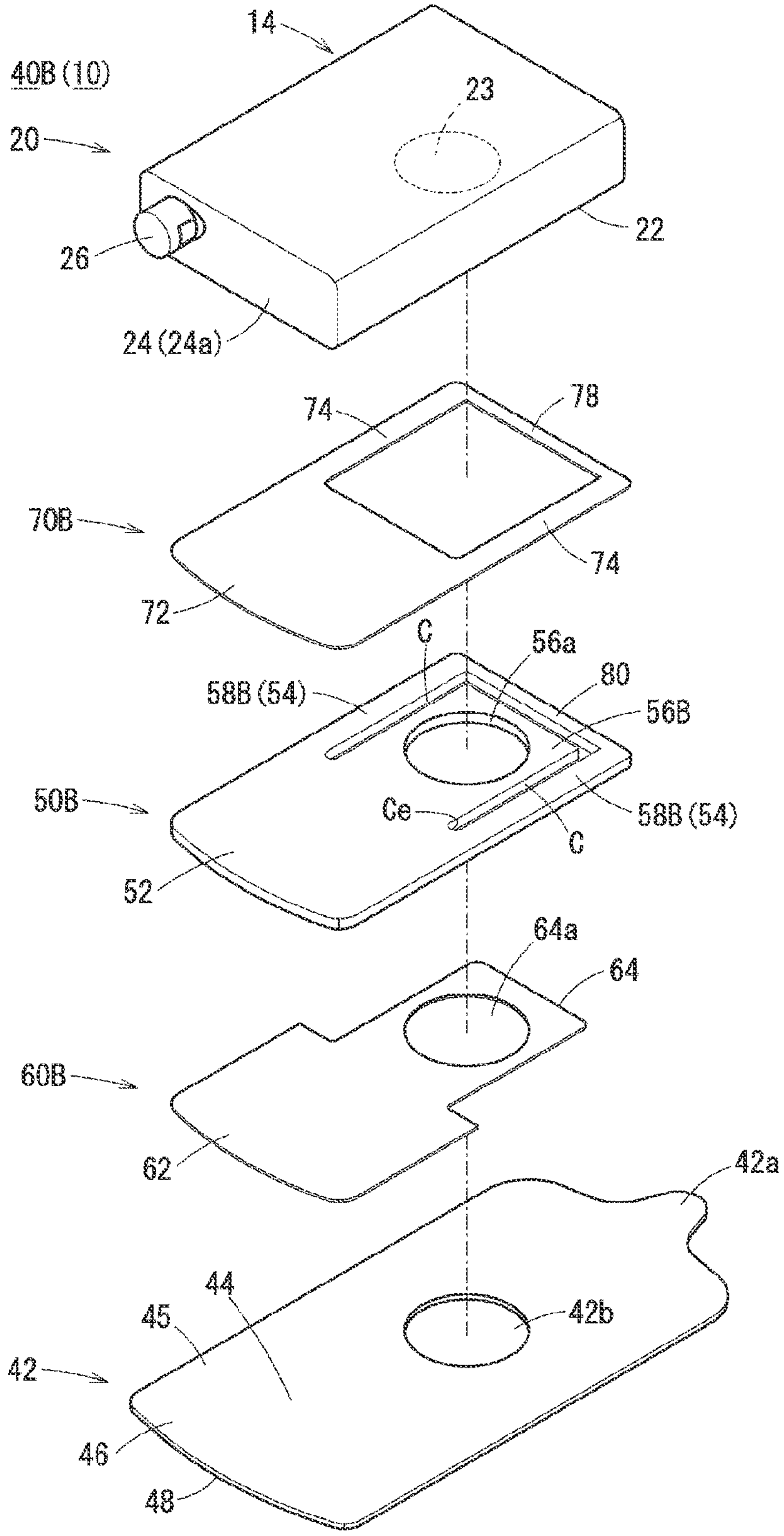
FIG. 6 is an exploded perspective view showing a medical apparatus according to a second modification.

A medical apparatus 40B (intermediate member 50B) of the indwelling device 10 according to a second modification shown in FIG. 6 is different from the medical apparatus 40, 40A in that a central piece 56B extends short, and extending ends (the other ends) of a pair of arm pieces 58B are coupled to each other by a bridge portion 80. A lower adhesive body 60B is formed in the same shape as the medical apparatus 40 described above, while an upper adhesive body 70B has a bridge portion attaching region 78 which is continuous with the pair of upper elastic piece attaching regions 74 and faces the bridge portion 80.

As a result, in the medical apparatus 40B, the pair of arm pieces 58B and the bridge portion 80 can be more firmly fixed to the main body 14 (case 20). Therefore, the possibility that the intermediate member 50B is peeled off from the main body 14 due to the external force is further reduced while obtaining the same effect as the above-described medical apparatus 40. In other words, the shape of the portion (elastic piece 54) of the indwelling device 10 extending from the base 52 is not particularly limited, and various shapes may be adopted in consideration of the attaching range of the main body 14 or the main-body-side attaching sheet 42.

Third Modification

Figure 7:
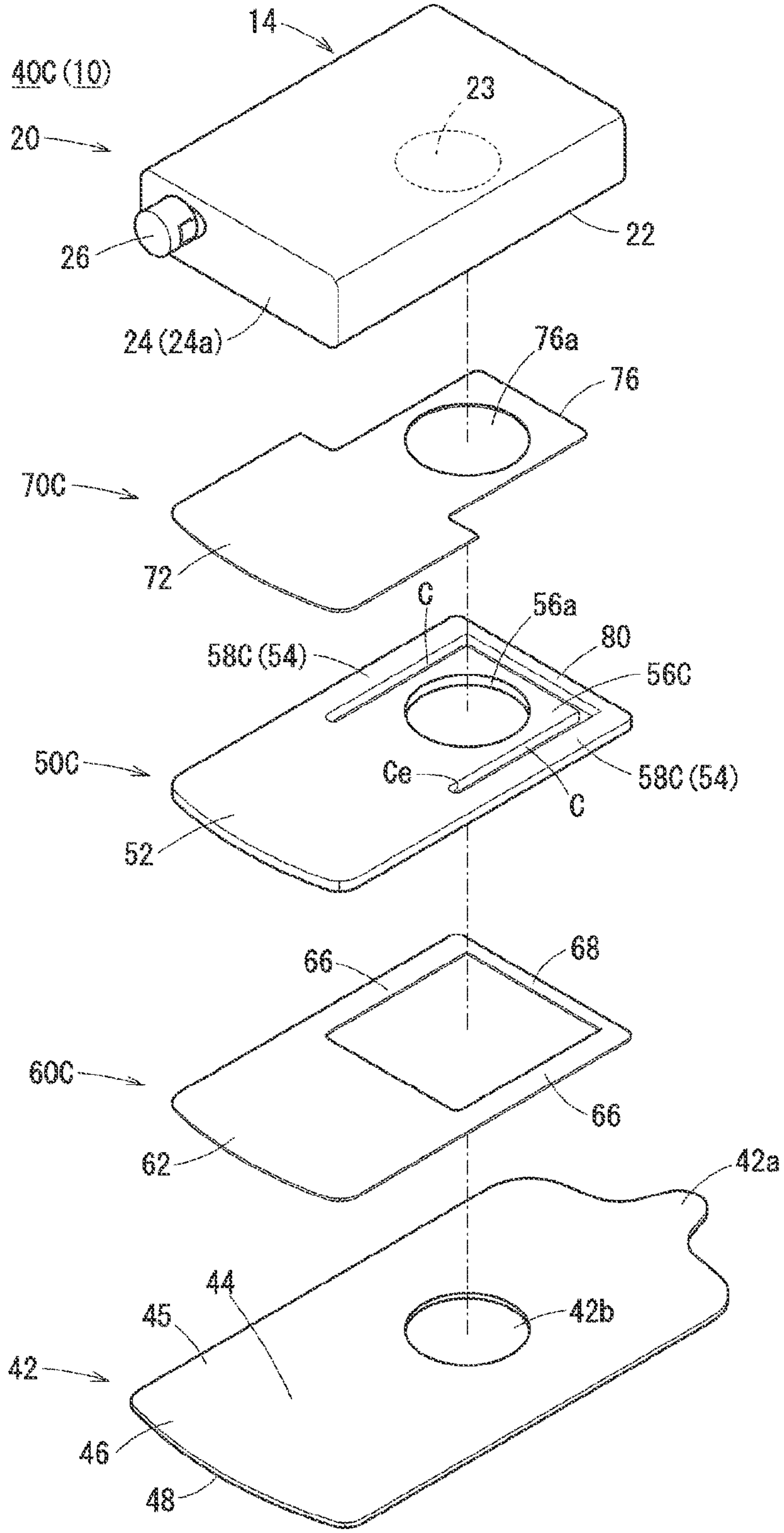
FIG. 7 is an exploded perspective view showing a medical apparatus according to a third modification.

A medical apparatus 40C (intermediate member 50C) of the indwelling device 10 according to a third modification shown in FIG. 7 is different from the medical apparatus 40, 40A, 40B in that an intermediate member 50C having the same shape as the intermediate member 50B is applied, a central piece 56C is fixed to the main body 14, and a pair of arm pieces 58C and the bridge portion 80 are fixed to the main-body-side attaching sheet 42 via a lower adhesive body 60C. In this case, the central piece 56C is fixed to the main body 14 via an upper adhesive body 70C, and the pair of arm pieces 58C and the bridge portion 80 are fixed to the main-body-side attaching sheet 42 via a lower adhesive body 60C having the bridge portion attaching region 68 continuous with the pair of lower elastic piece attaching regions 66. Even with this configuration, the possibility that the intermediate member 50C is peeled off from the main-body-side attaching sheet 42 by an external force is further reduced while obtaining the same effect as the above-described medical apparatus 40.

Fourth Modification

Figure 8A:
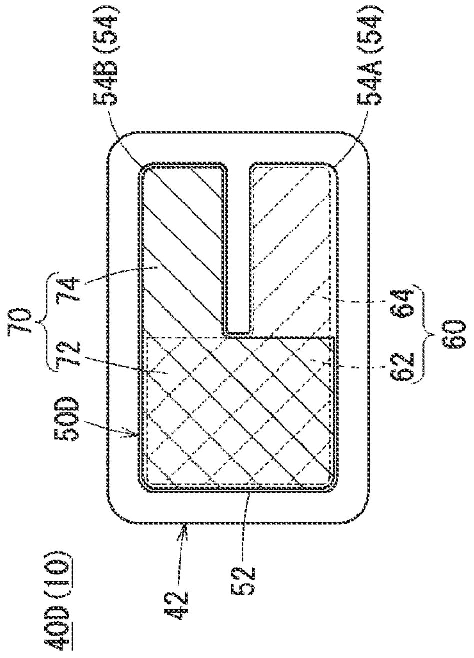
FIG. 8A is a plan view showing a medical apparatus according to a fourth modification.

A medical apparatus 40D (intermediate member 50D) of the indwelling device 10 according to a fourth modification shown in FIG. 8A has two elastic pieces 54 extending in parallel and in the same direction from the base 52. One elastic piece 54A constitutes a first extending portion fixed to the main-body-side attaching sheet 42, and the other elastic piece 54B constitutes a second extending portion fixed to the main body 14. The indwelling device 10 can obtain the same effect as that of the medical apparatus 40 even if the medical apparatus 40D is configured as described above.

Fifth Modification

Figure 8B:
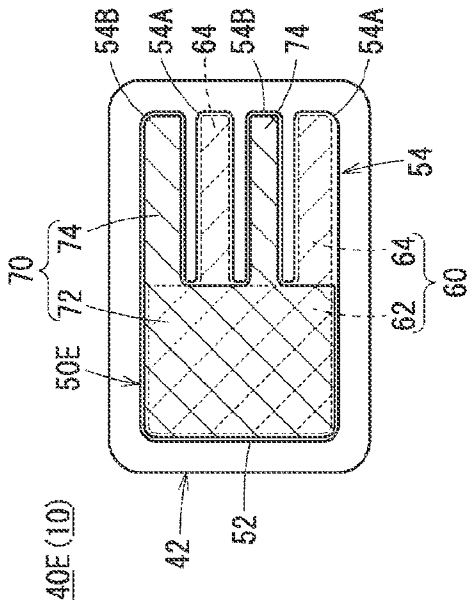
FIG. 8B is a plan view showing a medical apparatus according to a fifth modification.

A medical apparatus 40E (intermediate member 50E) of the indwelling device 10 according to a fifth modification shown in FIG. 8B has four elastic pieces 54 extending in parallel and in the same direction from the base 52. In this case, the plurality of elastic pieces 54 may be alternately provided with a first extending portion (elastic piece 54A) fixed to the main-body-side attaching sheet 42 and a second extending portion (elastic piece 54B) fixed to the main body 14. In short, the number of the elastic pieces 54 provided in the intermediate members 50 and 50A to 50E can be varied as desired.

Sixth Modification

Figure 8C:
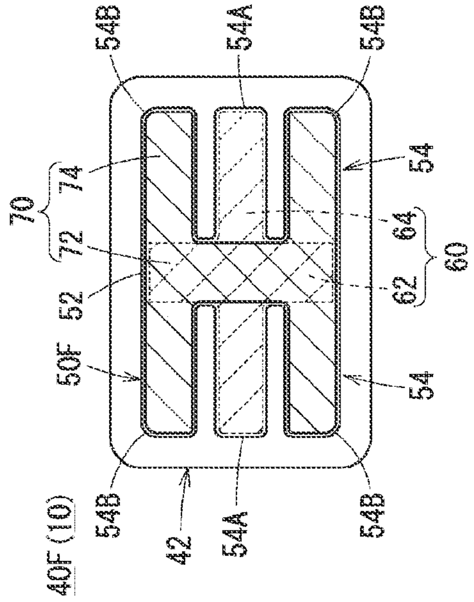
FIG. 8C is a plan view showing a medical apparatus according to a sixth modification.

A medical apparatus 40F (intermediate member 50F) of the indwelling device 10 according to a sixth modification shown in FIG. 8C has the base 52 at a central portion in the longitudinal direction. The medical apparatus 40F has a plurality of elastic pieces 54 extending in one end direction from the base 52 and a plurality of elastic pieces 54 extending in the other end direction from the base 52. Each of the plurality of elastic pieces 54 on one end side and the other end side has a first extending portion (elastic piece 54A) fixed to the main-body-side attaching sheet 42 and a second extending portion (elastic piece 54B) fixed to the main body 14. Even with such a configuration, the indwelling device 10 can be placed and held on the curved body surface. The plurality of elastic pieces 54 are not limited to extend in the longitudinal direction of the intermediate members 50, 50A to 50F, and may extend in the lateral direction.

Seventh Modification

Figure 8D:
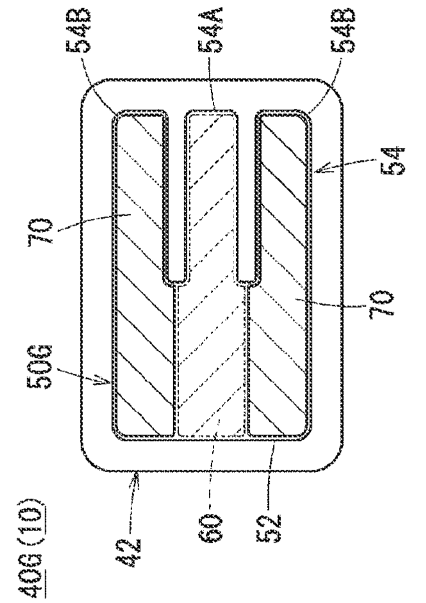
FIG. 8D is a plan view showing a medical apparatus according to a seventh modification.

A medical apparatus 40G (intermediate member 50G) of the indwelling device 10 according to a seventh modification shown in FIG. 8D has the base 52 and the plurality of elastic pieces 54, and has a first extending portion in which the base 52 is fixed to the main-body-side attaching sheet 42 and a second extending portion fixed to the main body 14. As described above, the intermediate member 50G can reinforce fixing between the main body 14 and the main-body-side attaching sheet 42 even if the lower adhesive body 60 and the upper adhesive body 70 do not have a portion overlapping in the vertical direction.

An indwelling device 10 according to one aspect includes a main body 14, a sheet-like or sheet-shaped attaching member (main-body-side attaching sheet 42) for holding the main body on a body surface of a living body, and plate-like or plate-shaped intermediate members 50, 50A to 50G that are configured to be elastically deformable and are stacked between the main body 14 and the attaching member, in which the intermediate members 50, 50A to 50G include a base 52 and a first extending portion (central piece 56, arm piece 58A) and a second extending portion (central piece 56A, arm piece 58) extending in parallel from the base 52, a first fixing portion (lower adhesive bodies 60, 60A to 60C) fixed to the attaching member from the base 52 to the first extending portion is provided on a surface of the intermediate members 50, 50A to 50G on the attaching member side, a second fixing portion (upper adhesive bodies 70, 70A to 70C) fixed to the main body 14 from the base 52 to the second extending portion is provided on a surface of the intermediate members 50, 50A to 50G on the main body 14 side, the first extending portion is not fixed to the main body 14, and the second extending portion is not fixed to the attaching member.

According to the above, the indwelling device 10 can stably hold or position the main body 14 on the body surface of the living body by the simple configuration in which the intermediate members 50, 50A to 50G are provided between the main body 14 and the attaching member (main-body-side attaching sheet 42). That is, in the indwelling device 10 in a state of being positioned on the body surface, the first extending portion (central piece 56, arm piece 58A) fixed to the attaching member follows the body surface without following the main body 14, and the second extending portion (central piece 56A, arm piece 58) fixed to the main body 14 can be separated from the body surface. Therefore, even if an external force is applied to the main body 14, the intermediate members 50, 50A to 50G elastically deform to absorb the external force while maintaining the fixing between the first fixing portion (lower adhesive bodies 60, 60A to 60C) and the attaching member and the fixing between the second fixing portion (upper adhesive body 70, 70A to 70C) and the main body 14. Therefore, even in a case where the indwelling device 10 is held on or adhered to the body surface for a long period of time, it is possible to maintain the attached state while suppressing the attaching state of the attaching member from becoming defective.

The first fixing portion (lower adhesive bodies 60, 60A to 60C) is provided on the entire surface of the base 52 on the attaching member (main-body-side attaching sheet 42) side, and the second fixing portion (upper adhesive bodies 70, 70A to 70C) is provided on the entire surface of the base 52 on the main body 14 side. As a result, the intermediate members 50, 50A to 50G can firmly hold the main body 14 at the base 52.

The intermediate members 50, 50A to 50E are formed in a rectangular shape coinciding with the fixing target place of the main body 14 in plan view, have the base 52 on one end side in the longitudinal direction, and have the first extending portion (central piece 56, arm piece 58A) and the second extending portion (central piece 56A, arm piece 58) on the other end side in the longitudinal direction. The rectangular main body 14 is easily peeled off along the longitudinal direction in the attached state, but since the indwelling device 10 has the first extending portion and the second extending portion on the other end side in the longitudinal direction as described above, it is possible to suppress peeling of the main body 14 from the longitudinal direction.

One of the first extending portion (central piece 56, arm piece 58A) and the second extending portion (central piece 56A, arm piece 58) is a central piece 56, 56A protruding from a central portion of the base 52 in the width direction, and the other of the first extending portion and the second extending portion is a pair of arm pieces 58, 58A protruding from both sides of the base 52 in the width direction. As a result, the indwelling device 10 can further stabilize the fixing of the intermediate members 50, 50A to 50C to the attaching member (main-body-side attaching sheet 42) and the main body 14.

The pair of arm pieces 58, 58A includes a bridge portion 80 that bridges the protruding ends of the arm pieces. As a result, the intermediate members 50B, 50C can more firmly fix the pair of arm pieces 58, 58A and the bridge portion 80 to the attaching member (main-body-side attaching sheet 42) or the main body 14.

A clearance C is provided between the first extending portion (central piece 56, arm piece 58A) and the second extending portion (central piece 56A, arm piece 58) adjacent to each other, and the clearance C has an arc-shaped edge portion Ce at a portion where the first extending portion and the second extending portion are coupled to the base 52. As a result, an external force that tears the first extending portion and the second extending portion is applied to the intermediate members 50, 50A to 50G, so that it is possible to suppress the damage at the edge portion Ce and maintain the attached state preferably.

The main body 14 has the operation unit 23 for operating the main body 14 on a surface facing the intermediate members 50, 50A to 50C, the intermediate members 50, 50A to 50C have an exposure portion (intermediate member side exposure hole 56*a*) for exposing the operation unit 23 at a position facing the operation unit 23, and the exposure portion is provided in either the first extending portion (central piece 56) or the second extending portion (central piece 56A). As a result, the indwelling device 10 can reliably operate the operation unit 23 even in the configuration including the intermediate members 50, 50A to 50C. In particular, even after the user forgets to operate the operation unit 23 and attaches the main body 14 on the body surface, if the operation unit 23 is at the position of the first extending portion or the second extending portion, it is possible to operate the operation unit 23 while exposing the operation unit 23 without peeling the attaching member (the main-body-side attaching sheet 42) from the body surface.

The indwelling device 10 is a drug administration device 12 that administers a drug to a living body, and the base 52 is disposed at a position near an outflow portion of the drug of the main body 14. As a result, the drug administration device 12 can firmly hold the drug outflow portion of the main body 14 at the base 52 of the intermediate members 50, 50A to 50E, 50G.

The detailed description above describes embodiments of a medical apparatus and indwelling device representing examples of the inventive medical apparatus and indwelling device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical apparatus to be positioned on a surface of a living body comprising:

a main body;

a sheet-shaped attaching member for indwelling the main body on the surface of the living body;

a plate-shaped intermediate member that is configured to be elastically deformable and is stacked between the main body and the attaching member;

the intermediate member including a base, and a first extending portion and a second extending portion that extend in parallel from the base;

a first fixing portion fixed to the attaching member from the base to the first extending portion, the first fixing portion being provided on a surface of the intermediate member on a side of the attaching member;

a second fixing portion fixed to the main body from the base to the second extending portion, the second fixing portion being provided on a surface of the intermediate member on a side of the main body;

the first extending portion is not fixed to the main body;

the second extending portion is not fixed to the attaching member; and wherein one of the first extending portion and the second extending portion is a central piece protruding from a central portion in a width direction of the base, and wherein another one of the first extending portion and the second extending portion is a pair of arm pieces protruding from both sides in the width direction of the base.

2. The medical apparatus according to claim 1, wherein the first fixing portion is provided on an entire surface of the base on a side of the attaching member, and wherein the second fixing portion is provided on an entire surface of the base on a side of the main body.

3. The medical apparatus according to claim 1, wherein the intermediate member is a rectangular-shaped intermediate member coinciding in shape with a shape of a fixing target place of the main body in plan view, the rectangular-shaped intermediate member being elongated in a longitudinal direction, and wherein the intermediate member includes the base on one end side in the longitudinal direction, and the first extending portion and the second extending portion on another end side in the longitudinal direction.

4. The medical apparatus according to claim 1, wherein the pair of arm pieces includes a bridge portion that bridges protruding ends of the pair of arm pieces.

5. The medical apparatus according to claim 1, wherein a clearance is provided between the first extending portion and the second extending portion adjacent to each other, and wherein the clearance has an arc-shaped edge portion at a portion where the first extending portion and the second extending portion are coupled to the base.

6. The medical apparatus according to claim 1, wherein the main body includes an operation unit that is operable by a user to operate the main body, the operation unit being on a surface of the main body facing the intermediate member, wherein the intermediate member includes an exposure portion for exposing the operation unit at a position facing the operation unit, and wherein the exposure portion is provided in either the first extending portion or the second extending portion.

7. The medical apparatus according to claim 1, wherein the indwelling device is a drug administration device that administers a drug to the living body, and wherein the base is disposed at a position near an outflow portion of the drug of the main body.

8. A medical apparatus to be placed on a surface of a living body comprising:

a main body possessing a lower surface;

an attaching sheet possessing an upper surface and a lower surface, the upper surface of the attaching sheet facing towards the lower surface of the main body, the lower surface of the attaching sheet being provided with an adhesive to adhere to the surface of the living body;

an elastically deformable intermediate member positioned between the attaching sheet and the main body, the intermediate member being positioned in a plane and including an upper surface facing towards the main body and a lower surface facing towards the attaching sheet;

the intermediate member including a base, the intermediate member also including first and second extending portions that extend away from the base and that are parallel to one another, the first and second extending portions being movable relative to one another and in opposite directions out of the plane;

a first fixing portion positioned between the intermediate member and the attaching sheet, the first fixing portion being fixed to at least a part of the upper surface of the attaching sheet and to the lower surface of the base of the intermediate member so that the base of the intermediate member is fixed to the attaching sheet;

a second fixing portion positioned between the intermediate member and the main body, the second fixing portion being fixed to at least a part of the upper surface of the base of the intermediate member and to the lower surface of the main body so that the base of the intermediate member is fixed to the main body;

the first extending portion is fixed to the attaching sheet and is movable relative to the main body;

the second extending portion is fixed to the main body and is movable relative to the attaching member; and wherein one of the first extending portion and the second extending portion is a central piece protruding from a central portion in a width direction of the base, and wherein another one of the first extending portion and the second extending portion is a pair of arm pieces protruding from both sides in the width direction of the base.

9. The medical apparatus according to claim 8, wherein the first fixing portion is fixed to an entirety of the lower surface of the base of the intermediate member, and wherein the second fixing portion is fixed to an entirety of the upper surface of the base of the intermediate member.

10. The medical apparatus according to claim 8, wherein the intermediate member is an elongated intermediate member that is elongated in a longitudinal direction, the base of the intermediate member being located at one longitudinal end of the elongated intermediate member, the first extending portion and the second extending portion extending away from the base in the longitudinal direction.

11. The medical apparatus according to claim 8, wherein the intermediate member is elongated and extends in a longitudinal direction from one longitudinal end of the intermediate member toward an opposite longitudinal end of the intermediate member, the first extending portion and the second extending portion extending away from the base in the longitudinal direction, the first extending portion and the second extending portion each possessing a side surface that extends in the longitudinal direction, the side surface of the first extending portion that extends in the longitudinal direction facing the side surface of the second extending portion that extends in the longitudinal direction.

12. The medical apparatus according to claim 8, wherein the second extending portion is the pair of arm pieces, the pair of arm pieces extending away from the base and being flexible and spaced apart from each other, and the first extending portion is the central piece, the central piece being positioned between the pair of spaced apart flexible arm pieces.

13. The medical apparatus according to claim 12, wherein the two flexible arm pieces that extend away from the base have free ends located farthest from the base, and the flexible central piece that extends away from the base has a free end located farthest from the base.

14. The medical apparatus according to claim 12, wherein the two flexible arm pieces that extend away from the base have ends located farthest from the base, the flexible central piece that extends away from the base has a free end located farthest from the base, the ends of the two flexible arm pieces located farthest from the base being connected to one another by a bridge.

15. The medical apparatus according to claim 8, wherein the intermediate member is elongated and extends in a longitudinal direction from one longitudinal end of the intermediate member toward an opposite longitudinal end of the intermediate member, the first extending portion and the second extending portion extending away from the base in the longitudinal direction, the first extending portion and the second extending portion each possessing a side surface that extends in the longitudinal direction, the side surface of the first extending portion that extends in the longitudinal direction facing towards and being spaced apart from the side surface of the second extending portion that extends in the longitudinal direction so that a clearance exists between the side surface of the first extending portion and the side surface of the second extending portion.

16. The medical apparatus according to claim 8, wherein the main body includes an operation button that is operable by a user to operate the main body, the intermediate member and the attaching sheet both including a through hole through which passes the operation button.

17. A drug administration device comprising:

a drug supply source;

a tube connectable to the drug supply source; and an administration unit connectable to the tube and configured to administer a drug from the drug supply source and through the tube when the tube is connected to both the drug supply source and the administration unit;

the drug supply source comprising:

a main body possessing a lower surface to face toward a surface of a living body;

an attaching sheet possessing an upper surface and a lower surface, the upper surface of the attaching sheet facing towards the lower surface of the main body, the lower surface of the attaching sheet being adapted to face towards the surface of the living body;

an elastically deformable intermediate member positioned between the main body and the attaching sheet;

the intermediate member including a base, a first extending portion and a second extending portion, the first and second extending portions extending parallel to one another and away from the base;

a first fixing portion fixed to a lower surface of the base of the intermediate member and to the upper surface of the attaching sheet;

a second fixing portion fixed to an upper surface of the base of the intermediate member and to the lower surface of the main body;

the first extending portion being not fixed to the main body;

the second extending portion being not fixed to the attaching member; and wherein one of the first extending portion and the second extending portion is a central piece protruding from a central portion in a width direction of the base, and wherein another one of the first extending portion and the second extending portion is a pair of arm pieces protruding from both sides in the width direction of the base.

18. The drug administration device according to claim 17, wherein the first fixing portion is fixed to an entirety of the lower surface of the base of the intermediate member, and wherein the second fixing portion is fixed to an entirety of the upper surface of the base of the intermediate member.

19. The drug administration device according to claim 17, wherein the intermediate member is an elongated intermediate member that is elongated in a longitudinal direction, the base of the intermediate member being located at one longitudinal end of the elongated intermediate member, the first extending portion and the second extending portion extending away from the base in the longitudinal direction.

20. A method comprising:

performing a medical procedure on the patient;

indwelling an administration unit on a body surface of the patient after the performing of the medical procedure on the patient;

connecting the administration unit to a drug supply source, the drug supply source containing a drug and comprising:

a main body possessing a lower surface; an attaching sheet possessing an upper surface and a lower surface, the upper surface of the attaching sheet facing towards the lower surface of the main body; an elastically deformable intermediate member positioned between the main body and the attaching sheet, the intermediate member including a base possessing upper and lower surfaces, a first extending portion and a second extending portion, the first and second extending portions extending parallel to one another and away from the base; a first fixing portion fixed to the lower surface of the base of the intermediate member and to the upper surface of the attaching sheet; a second fixing portion fixed to the upper surface of the base of the intermediate member and to the lower surface of the main body; the first extending portion being not fixed to the main body; the second extending portion being not fixed to the attaching member; and wherein one of the first extending portion and the second extending portion is a central piece protruding from a central portion in a width direction of the base, and wherein another one of the first extending portion and the second extending portion is a pair of arm pieces protruding from both sides in the width direction of the base, placing the main body of the drug supply source on the body surface of the patient, the placing of the main body of the drug supply source on the body surface of the patient occurring before or after the connecting of the administration unit to the drug supply source; and administering the drug from the drug supply source to the patient by way of the administration unit that is indwelled on the body surface of the patient.

21. A method according to claim 20, further comprising starting the administering of the drug solution to the patent after a predetermined time has elapsed after finishing the medical procedure, the predetermined time being at least 0.5 hour.

* * * * *